United States Patent
Trilisky et al.

(10) Patent No.: US 11,409,786 B2
(45) Date of Patent: Aug. 9, 2022

(54) SYSTEMS AND METHODS FOR COMPUTER-ASSISTED SEARCH OF IMAGE SLICES FOR INDICATIONS OF A FINDING

(71) Applicants: KONINKLIJKE PHILIPS N.V., Eindhoven (NL); THE UNIVERSITY OF CHICAGO, Chicago, IL (US)

(72) Inventors: Igor Trilisky, Eindhoven (NL); Merlijn Sevenster, Haarlem (NL); Amir Mohammad Tahmasebi Maraghoosh, Arlington, MA (US); Paul Joseph Chang, Chicago, IL (US)

(73) Assignees: KONINKLIJKE PHILIPS N.V., Eindhoven (NL); THE UNIVERSITY OF CHICAGO, Chicago, IL (US)

( * ) Notice: Subject to any disclaimer, the term of this patent is extended or adjusted under 35 U.S.C. 154(b) by 200 days.

(21) Appl. No.: 16/605,517

(22) PCT Filed: Apr. 20, 2018

(86) PCT No.: PCT/EP2018/060183
§ 371 (c)(1),
(2) Date: Oct. 16, 2019

(87) PCT Pub. No.: WO2018/193089
PCT Pub. Date: Oct. 25, 2018

(65) Prior Publication Data
US 2020/0125598 A1    Apr. 23, 2020

Related U.S. Application Data

(60) Provisional application No. 62/487,675, filed on Apr. 20, 2017.

(51) Int. Cl.
*G06F 16/535*    (2019.01)
*G06F 16/583*    (2019.01)
(Continued)

(52) U.S. Cl.
CPC .......... *G06F 16/535* (2019.01); *G06F 16/583* (2019.01); *G06V 10/457* (2022.01); *G06F 3/14* (2013.01)

(58) Field of Classification Search
CPC . A61B 5/055; A61B 2090/103; A61B 6/5211; A61B 6/466; G06F 19/00; G06F 16/5866; G06F 40/16
See application file for complete search history.

(56) References Cited

U.S. PATENT DOCUMENTS 4,945,478 A * 7/1990 Merickel ................ A61B 5/055
382/131
5,715,334 A * 2/1998 Peters ...................... G06T 5/50
382/130
(Continued)

FOREIGN PATENT DOCUMENTS

WO    2018069201    4/2018

OTHER PUBLICATIONS

International Search Report and Written Opinion dated Jul. 11, 2018 for International Application No. PCT/EP2018/060183 filed Apr. 20, 2018.

*Primary Examiner* — Angelica Ruiz

(57) ABSTRACT

The present disclosure pertains to computer-assisted search of image slices. In some embodiments, an image slice having a detected finding (and representing a cross section of at least a portion of an individual) may be determined. A search space may be reduce to a subset of image slices respectively representing a cross section corresponding to the cross section represented by the determined image slice. The search space reduction may comprise filtering a set of image slices based on the cross section represented by the determined image slice. Image slice information related to the determined image slice and related one or more image slices (of the image slices subset) may be obtained based on (Continued)

the search space reduction. A determination of whether indications of the detected finding exist in the image slices (of the image slices subset) may be effectuated based on the image slice information.

19 Claims, 5 Drawing Sheets

(51) Int. Cl.
*G06V 10/44* (2022.01)
*G06F 3/14* (2006.01)

(56) References Cited

U.S. PATENT DOCUMENTS

| | | |
|---|---|---|
| 9,370,305 B2 | 6/2016 | Qian |
| 2003/0013951 A1 | 1/2003 | Stefanescu |
| 2011/0044523 A1* | 2/2011 | Gloger .................... G06T 7/143 |
| | | 382/131 |
| 2012/0093384 A1* | 4/2012 | Goto .................... G01R 33/543 |
| | | 382/131 |
| 2015/0261915 A1* | 9/2015 | Yanagida ............... G16H 30/20 |
| | | 382/131 |
| 2015/0262014 A1* | 9/2015 | Iwamura ................ G16H 50/20 |
| | | 382/128 |
| 2016/0048987 A1 | 2/2016 | Sevenster |
| 2016/0300351 A1* | 10/2016 | Gazit ...................... G06T 7/187 |
| 2016/0338613 A1* | 11/2016 | Beckers ............... A61B 5/7257 |
| 2018/0338741 A1* | 11/2018 | Lyman ................ A61B 6/5217 |
| 2019/0252061 A1 | 8/2019 | Chang |
| 2019/0259494 A1 | 8/2019 | Sevenster |

* cited by examiner

SYSTEMS AND METHODS FOR COMPUTER-ASSISTED SEARCH OF IMAGE SLICES FOR INDICATIONS OF A FINDING

CROSS REFERENCE TO RELATED APPLICATIONS

This application is the U.S. National Phase application under 35 U.S.C. § 371 of International Application No. PCT/EP2018/060183 filed Apr. 20, 2018, published as WO 2018/193089 on Oct. 25, 2018, which claims the benefit of U.S. Provisional Patent Application No. 62/487,675 filed Apr. 20, 2017. These applications are hereby incorporated by reference herein.

BACKGROUND

1. Field

The present disclosure relates to systems and methods for facilitating computer-assisted search of image slices for indications of a finding.

2. Description of the Related Art

Advances in medical imaging techniques involving computed tomography (CT), Magnetic resonance imaging (MRI), mammography, or other technologies have enabled physicians, clinicians, or other service providers to help patients detect various medical conditions (e.g., tumors or other masses) in their early stages, as well as perform close monitoring of such medical conditions as they develop inside the patients' bodies. Moreover, improvements in processing power, memory and storage capacity, or other resources in computer systems has enabled physicians or other users to more easily capture or obtain medical images (e.g., medical image slices or other images), videos, or other items related to patients, and more quickly search and identify the images, videos, or other items of relevance to such users.

As an example, if a physician observes a particular finding (e.g., a tumor or other mass) in one or more image slices captured during a recent examination of a patient, the physician may utilize a computer system in communication with a database of image slices from prior examinations of the patient to search the database for image slices with one or more indications of the particular finding to determine whether the particular finding is a new development or whether the particular finding was simply undetected during prior examinations. However, given the size of the images and other related items generated by typical medical imaging techniques (e.g., due to the high resolution of such imaging) and the large number of images generated for a single patient, searching a database of images associated with a patient to automatically identify the patient's images that might show evidence of a newly discovered finding can be extremely time-consuming and inefficient (e.g., especially if conducted on a set of image slices that include image slices from multiple prior examinations). These and other drawbacks exist.

SUMMARY

Accordingly, one aspect of the disclosure relates to a system for facilitating computer-assisted search of image slices for indications of a finding. The system includes one or more processors and/or other components. The one or more processors are configured by machine-readable instructions to: determine an image slice that includes a detected finding related to an individual, the determined image slice representing a cross section of at least a portion of the individual during an examination of the individual; reduce a search space to a subset of image slices including image slices that respectively represent a cross section corresponding to the cross section represented by the determined image slice, wherein reducing the search space includes filtering a set of image slices based on the cross section represented by the determined image slice, the image slices set including image slices that respectively represent a cross section of at least a portion of the individual during one or more other examinations of the individual; obtain first image slice information related to the determined image slice; obtain, based on the search space reduction, second image slice information related to one or more image slices of the image slices subset; and determine, based on the first image slice information and the second image slice information, whether one or more indications of the detected finding exist in the one or more image slices of the image slices subset.

Another aspect of the disclosure relates to a method for facilitating computer-assisted search of image slices for indications of a finding. The method includes: determining an image slice that includes a detected finding related to an individual, the determined image slice representing a cross section of at least a portion of the individual during an examination of the individual; reducing a search space to a subset of image slices including image slices that respectively represent a cross section corresponding to the cross section represented by the determined image slice, wherein reducing the search space includes filtering a set of image slices based on the cross section represented by the determined image slice, the image slices set including image slices that respectively represent a cross section of at least a portion of the individual during one or more other examinations of the individual; obtaining first image slice information related to the determined image slice; obtaining, based on the search space reduction, second image slice information related to one or more image slices of the image slices subset; and determining, based on the first image slice information and the second image slice information, whether one or more indications of the detected finding exist in the one or more image slices of the image slices subset.

Another aspect of the disclosure relates to a system for facilitating computer-assisted search of image slices for indications of a finding. The system includes: means for determining an image slice that includes a detected finding related to an individual, the determined image slice representing a cross section of at least a portion of the individual during an examination of the individual; means for reducing a search space to a subset of image slices including image slices that respectively represent a cross section corresponding to the cross section represented by the determined image slice, wherein reducing the search space includes filtering a set of image slices based on the cross section represented by the determined image slice, the image slices set including image slices that respectively represent a cross section of at least a portion of the individual during one or more other examinations of the individual; means for obtaining first image slice information related to the determined image slice; means for obtaining, based on the search space reduction, second image slice information related to one or more image slices of the image slices subset; and means for determining, based on the first image slice information and the second image slice information, whether one or more indications of the detected finding exist in the one or more image slices of the image slices subset.

These and other features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
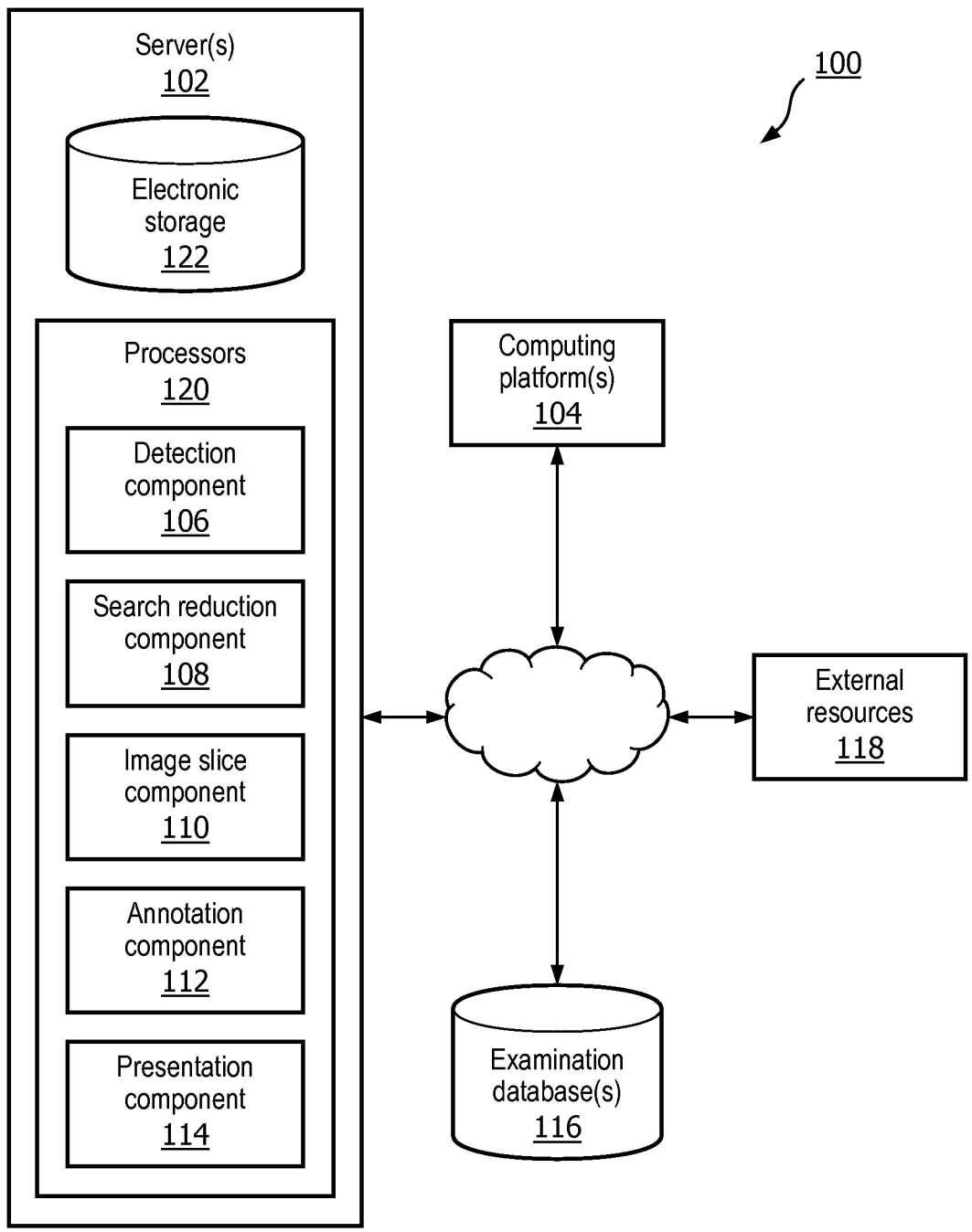
FIG. 1 illustrates a system configured for facilitating computer-assisted search of image slices for indications of a finding, in accordance with one or more embodiments.

As used herein, the singular forms of "a", "an", and "the" include plural references unless the context clearly dictates otherwise. As used herein, the term "or" means "and/or" unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 shows a system 100 configured for facilitating computer-assisted search of image slices for indications of a finding. In some embodiments, system 100 may include one or more servers 102. The server(s) 102 may be configured to communicate with one or more computing platforms 104 according to a client/server architecture, a peer-to-peer architecture, and/or other architectures. The users may access system 100 via computing platform(s) 104. The server(s) 102 may be configured to execute machine-readable instructions. The machine-readable instructions may include a detection component 106, a search reduction component 108, an image slice component 110, an annotation component 112, a presentation component 114, or other components.

As indicated above, although improvements in processing power, memory and storage capacity, or other resources in computer systems has enabled physicians, clinicians, or other users to more quickly search and identify relevant images, videos, or other items of relevance to such users, typical computer systems often fail to enable their users to search, obtain, and identify a patient's image slices having specific characteristics (e.g., evidence of a tumor/mass or other finding). In one use case, if a physician observes a particular finding (e.g., a tumor or other mass) in one or more image slices captured during a recent examination of a patient, the physician may utilize a computer system in communication with a database of image slices from prior examinations of the patient to search the database for image slices with one or more indications of the particular finding to determine whether the particular finding is a new development or whether the particular finding was simply undetected during prior examinations. However, given the size of the images and other related items generated by typical medical imaging techniques (e.g., due to the high resolution of such imaging) and the large number of images generated for a single patient, searching a database of images associated with a patient to automatically identify the patient's images that might show evidence of a newly discovered finding can be extremely time-consuming and inefficient.

In some embodiments, to reduce the time and/or the amount of computational resources (e.g., processing power, memory usage, etc.) for such a search and/or processing of search results therefrom, system 100 may reduce a search space from a larger set of an individual's image slices (e.g., captured during one or more examinations of the individual) to a smaller subset of the larger set of the individual's image slices. Information related to the image slices of the reduced, smaller subset may be obtained and processed to automatically identify the most relevant ones of the image slices for the user. As used herein, an image slice may include an image representing a cross section of at least a portion of one or more items (e.g., at least a portion of an individual or other item), a frame of a video representing a cross section of at least a portion of the items, or other aspect of media representing a cross section of at least a portion of the items.

In some embodiments, if a given image slice captured during a given examination of an individual is determined to have a particular finding (e.g., tumor/mass or other finding is shown in the given image slice), system 100 may automatically determine whether there is evidence of the particular finding in any image slices captured during one or more other examinations of the individual. As an example, system 100 may automatically detect evidence of the particular findings in other image slices based on a processing of the other image slices (e.g., based on one or more disease-specific recognition models, information related to a region (within the given image slice) that includes the particular finding, etc.). As another example, if the given image slice represents a specific cross section of at least a portion of the individual during the given examination, system 100 may automatically reduce a search space to a subset of image slices including image slices that respectively represent cross sections corresponding to the specific cross section, other cross sections adjacent or proximate the corresponding cross sections, or other cross sections. System 100 may perform the search space reduction by filtering a larger set of image slices based on the specific cross section (represented by the given image slice that shows the particular finding) to reduce the search space to the smaller subset of image slices. Other techniques, including those described herein in further detail below, for reducing the search space may additionally or alternatively be performed in some embodiments to increase the efficiency of such a search and/or processing of search results therefrom.

Figure 2A:
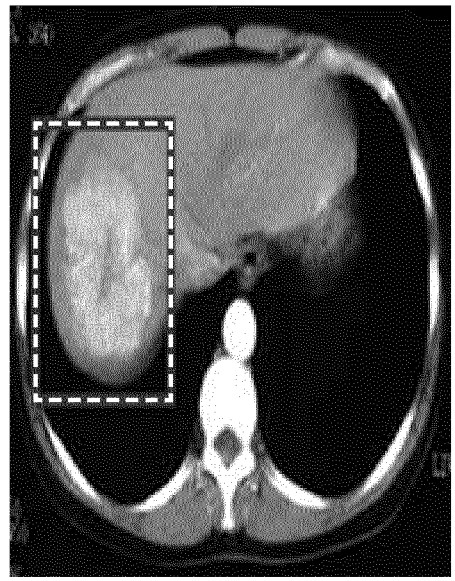
FIGS. 2a-2e illustrate image slices captured via different medical modalities, in accordance with one or more embodiments.
Figure 2B:
Figure 2C:
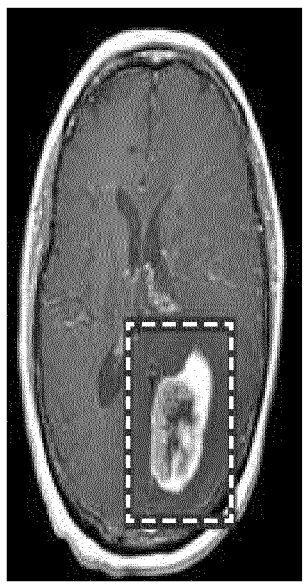
Figure 2D:
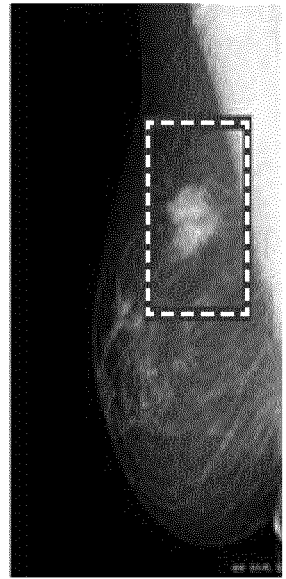

In some embodiments, detection component 106 may determine an image slice that includes a detected finding related to an individual. As an example, the determined image slice may represent a cross section of at least a portion of the individual during a given examination of the individual (e.g., a recent examination of the individual). The determined image slice may, for instance, be used as a reference image slice for searching a database of image slices and determining whether one or more indications of the detected finding exist in one or more other image slices representing at least a portion of the individual during one or more other examinations (e.g., prior to the given examination, subsequent to the given examination, etc.). As another example, FIGS. 2a, 2b, 2c, 2d show image slices depicting detected tumors/masses (e.g., as marked with rectangular boxes), where the image slices are captured via different imaging techniques. In one use case, FIG. 2a shows a mass of liver in a region of interest in a CT scan slice. FIG. 2b shows nodules in the lungs in a region of interest in the CT scan slice. FIG. 2c shows a tumor in a brain in a region of interest in a MRI scan slice. FIG. 2d shows a mass in a breast in a region of interest in an X-ray scan slice.

In some embodiments, detection component 106 may select an image slice (or a portion thereof) to be used as a reference image slice. In some embodiments, the selection of the image slice may be based on one or more user inputs, such as a user selection of the image slice, a user selection of a region within the image slice, or other user inputs. In some embodiments, the selection of the image slice may be based on a processing of image slices (e.g., associated with a recent examination of an individual) to automatically detect tumors or other findings. As an example, one or more disease-specific recognition models may be used to perform disease recognition on one or more sets of image slices to determine whether any of the image slices show evidence of specific diseases. In one scenario, a liver-tumor-specific model may be used to perform tumor recognition in image slices that represent cross sections of an individual's liver. A lung-tumor-specific model may be used to perform tumor recognition in image slices that represent cross sections of an individual's lung. A brain-tumor-specific model may be used to perform tumor recognition in image slices that represent cross sections of an individual's brain. A breast-tumor-specific model may be used to perform tumor recognition in image slices that represent cross sections of an individual's breast.

In some embodiments, search reduction component 108 may reduce a search space from a set of image slices to a subset of image slices. As an example, the image slices set may include image slices that respectively represent a cross section of at least a portion of an individual during one or more examinations. Search reduction component 108 may reduce the search space by filtering the image slices set based on information related to one or more reference image slices (e.g., image slices that are determined to include a tumor or other finding). In some embodiments, the image slices set may be filtered based on a given cross section represented by a reference image slice. As an example, the image slices set may be filtered such that the search space is reduced to a subset with (i) image slices that respectively represent a cross section corresponding to the given cross section, (ii) image slices that respectively represent a cross section adjacent or proximate the corresponding cross sections, or (3) other image slices. In one scenario, if a reference image slice is annotated as a Lung Cross Section X, where Lung Cross Section X is a particular cross section of an individual's lungs (e.g., a frontal view of the middle of the individual's lungs or other particular view), image slices that respectively represent a cross section corresponding to the cross section represented by the reference image slice may be image slices that respectively represent Lung Cross Section X. Image slices that respectively represent a cross section adjacent the corresponding cross section may be image slices that respectively represent Lung Cross Section X−1 or Lung Cross Section X+1. Image slices that respectively represent a cross section proximate the corresponding cross section may be image slices that respectively represent Lung Cross Sections X−Y to X+Y, where Y is a proximity threshold number used to determine the proximate cross sections. In embodiments in which the adjacent or proximate cross sections are included in the reduced space, a search may be performed on the three-dimensional views of the relevant portion of an individual while still decreasing the time and/or the amount of computational resources (e.g., processing power, memory usage, etc.) for such a search and/or processing of search results therefrom.

In some embodiments, search reduction component 108 may perform normalization of a given search space to prepare for reduction (or further reduction) of the space search. In one use case, search reduction component 108 may normalize the sequences of one or more multi-slice examinations onto a controlled nomenclature of sequence names (e.g., for each of the examinations represented in the given search space). In a further use case, this normalization step may take into account information from the sequence header. If the modalities at an institute are configured appropriately and the technician has received training, this information may be reliable and the normalization step can be implemented as a table mapping sequence header names onto the controlled nomenclature of sequence names. In another use case, parameter settings from the Digital Imaging and Communications in Medicine (DICOM) standards, image processing techniques, or other data can be leveraged.

In some embodiments, search reduction component 108 may register the image slices of matching sequences across multi-slice examinations. As an example, the registration may be based on taking the whole image volume (e.g., for each examination) into account (e.g., for more global matches across sequences) and/or based on the finding itself, such as a tumor, lesion, or other finding (e.g., to get more localized matching across different sequences). As an example, the registration could be based on either rigid or non-rigid methods or a combination of both.

Figure 2E:
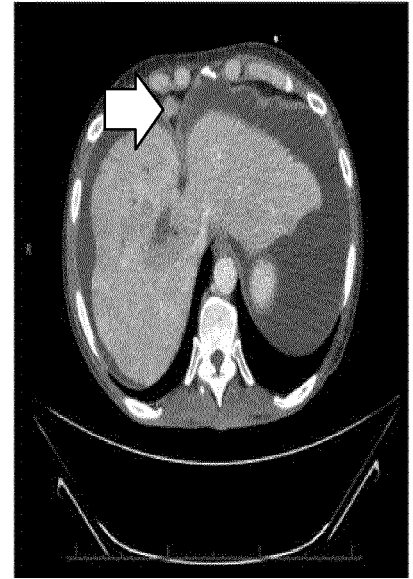

In some embodiments, search reduction component 108 may reduce a search space based on information related to a region (within a given image slice) that includes a detected finding. As an example, the region may include a user-defined region (e.g., where size or shape of the region is defined by a user), a region having a size or shape determined based on a size or shape of the detected finding, or other region. For example, FIGS. 2a, 2b, 2c, 2d show image slices with regions of interest marked in the form of rectangular boxes, each of which defines a two-dimensional region of interest surrounding the finding of an abnormality. The regions of interest may be drawn by a clinician (or other user), or the regions of interest may be automatically determined based on the size or shape of the respective abnormality or other criteria. It should be noted that, in some scenarios, a region of interest can be of any possible form, and annotation can be applied to the region of interest including text, symbols, or images (e.g., icon, GIF image, etc.). As discussed, in one use case, FIG. 2a shows a mass of liver in a region of interest in a CT scan slice. FIG. 2b shows nodules in the lungs in a region of interest in the CT scan slice. FIG. 2c shows a tumor in a brain in a region of interest in a MRI scan slice. FIG. 2d shows a mass in a breast in a region of interest in an X-ray scan slice. In another use case, FIG. 2e shows a schematic depiction of a lesion marked by a user, and this can be carried out through a standard measurement or as a structured finding object or differently, e.g., by double clicking or drawing a two-dimensional region of interest (e.g., a rectangular region, a circular region, etc.).

In some embodiments, search reduction component 108 may reduce a search space based on a size of a region (within a given image slice) that includes a detected finding, a shape of the region, a location of the region, or other criteria. In some embodiments, with respect to image slices captured during an examination of an individual, search reduction component 108 may reduce a search space to a subset of image slices that respectively represent a cross section corresponding to the given cross section or a cross section proximate the corresponding cross sections. As an example, search reduction component 108 may determine whether a cross section is in proximity of another cross section based on a predetermined proximity threshold. The predetermined proximity threshold may be a default proximity threshold, a user-defined proximity threshold, a relative threshold determined based on a type of the finding detected in the given image slice (e.g., type of tumor, mass, or other finding), a relative threshold determined based on a size or shape of a region that includes a finding of interest (e.g., tumor or other finding), or other threshold. In one scenario, if a reference image slice is annotated as a Lung Cross Section X, where Lung Cross Section X is a particular cross section of an individual's lungs (e.g., a frontal view of the middle of the individual's lungs or other particular view), the search space may be reduced to image slices that respectively represent Lung Cross Sections X−Y to X+Y, where Y is a proximity threshold number used to determine the proximate cross sections. In this way, for example, a search may be performed on the three-dimensional views of the relevant portion of an individual while still decreasing the time and/or the amount of computational resources (e.g., processing power, memory usage, etc.) for such a search and/or processing of search results therefrom.

In some embodiments, with respect to image slices captured during an examination of an individual, search reduction component 108 may reduce a search space to certain regions of the image slices within the search space. As an example, where a search space has already been reduced (e.g., via one or more techniques described herein), search reduction component may further reduce the search space to certain regions of the image slices within the reduced search space. As an example, the search space may be further reduced based on a location of a region of interest in a reference image slice (e.g., a location of the region of interest with respect to the individual's body, a location of the region of interest with respect to the reference image slice as a whole, etc.). In one use case, a reduced search space may be further reduced to regions of the image slices within the search space that correspond to the region of interest in the reference image slice. With respect to FIG. 2a, for example, a search space may be reduced to regions of image slices (with the search space) having the same or similar size, shape, and/or relative location as the region of the reference image slice shown in FIG. 2a (e.g., because the region of interest in the reference image slice is on the left side from the current perspective, the regions that remain in the reduced search space are regions in the left side on the remaining image slices).

In some embodiments, search reduction component 108 may reduce a search space by selecting, from a set of examinations, one or more examinations based on (i) a time of a given examination during which a reference image slice was captured, (ii) a time criteria, (iii) an individual for which at least a portion is represented by the reference image slice, (iv) an organ or area (of the individual) that is represented by the reference image slice, (v) or other criteria. Search reduction component 108 may reduce the search space such that the reduced search space is constrained to image slices captured during the selected examinations. In some embodiments, the reduced search space may be further reduced via one or more other techniques (e.g., as described herein). As an example, when a given image slice captured during a recent examination of an individual is detected to have a particular finding (e.g., a tumor or other finding), search reduction component 108 may select one or more other examinations from a set of examinations of that individual based on the selected examinations (i) being at least a predetermined threshold amount of time from the time at which the recent examination occurred, (ii) being at least a predetermined threshold amount of time from the times at which other ones of the selected examinations occurred, (iii) being examinations of an organ or area for which the recent examination was performed, or (iv) other criteria. As an example, one or more predetermined threshold amount of times (to be used to select which examinations should be included in a search space) may be a default threshold, a user-defined threshold, a relative threshold determined based on a type of the finding detected in the given image slice (e.g., type of tumor, mass, or other finding), a relative threshold determined based on a size or shape of the finding detected in the given image slice (e.g., size or shape of tumor, mass, or other finding), or other threshold.

In some embodiments, image slice component 110 may obtain information related to a reference image slice (e.g., determined to have a detected finding), information related to one or more image slices of a search space (e.g., a reduced search space derived via one or more techniques described herein), or other information. Based on the obtained information, image slice component 110 may determine whether one or more indications of the detected finding exist in the image slices of the search space. In some embodiments, each set of the obtained information may include information identifying characteristics related to the respective image slices. As an example, the information related to the reference image slice may include annotations associated with the reference image slice, characteristic vectors of objects represented in the reference image slice, or other information (e.g., data representing the pixels of the reference image slice or other data). As another example, the information related to the image slices of the search space may include annotations associated with the image slices, characteristic vectors of objects represented in the image slices, or other information (e.g., data representing the pixels of the image slices or other data). Annotations associated with an image slice may include annotations relevant to the image slice as a whole (e.g., a reference to an individual represented by the image slice, an organ or area of the individual that the image slice represents, an identification of the cross section represented by the image slice, etc.), annotations relevant only to specific to one or more regions of the image slice (e.g., size, shape, color, or other characteristics of tissue within the respective regions), or other annotations.

In some embodiments, image slice component 110 may compare annotations or characteristic vectors related to a reference image slice with annotations or characteristic vectors related to image slices (or specific regions thereof) of a search space (e.g., a reduced search space derived via one or more techniques described herein). Based on the comparison, image slice component 110 may determine whether one or more indications of a finding (e.g., detected in the reference image slice) exist in the image slices of the search space. In some embodiments, image slice component may compare the pixels or other data of the reference image slice (e.g., in a region of interest that includes the finding) with the pixels or other data of the image slices of the search space, and, based on the comparison, determine whether one or more indications of the finding exist in the image slices of the search space.

In some embodiments, image slice component 110 may use one or more disease-specific recognition models to perform disease recognition on one or more sets of image slices to determine whether one or more of the image slices show evidence of specific diseases. As an example, upon predicting a specific disease to which a finding in a reference image slice is related, a recognition model specific to the predicted disease may be used to perform recognition on the image slices of a search space to determine whether one or more indications of the finding exist in the image slices of the search space.

Figure 3A:
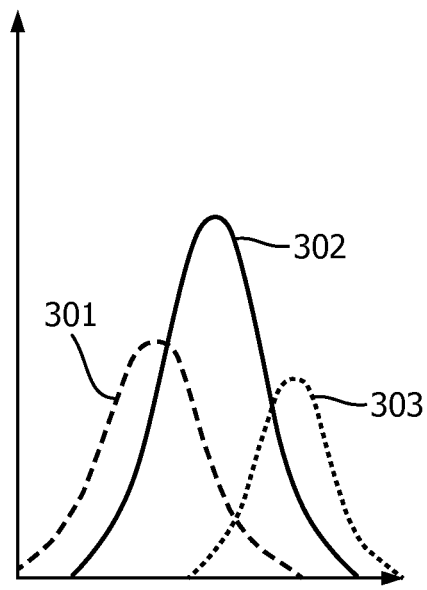
FIGS. 3a-3e illustrate graphical analyses of image slices, in accordance with one or more embodiments.
Figure 3B:
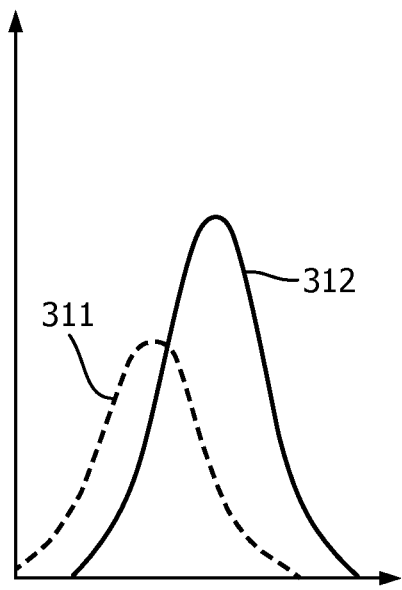

As an example, FIG. 3a shows an output of an image slice analysis performed on a reference image slice (e.g., an image slice in which tumor 303 was detected), and FIG. 3b shows an output of an image slice analysis performed on an image slice derived from a search of a reduced search space of image slices from other examinations. In one use case, the reference image slice may be associated with an examination at time t2, and the image slice derived from the search may be associated with an examination at time t1 (e.g., where time t1 is at least a predetermined threshold amount of time prior to time t2). The reference image slice in FIG. 3a shows normal tissues 301 and 302 and tumor 303. The image slice (in FIG. 3b) derived from the search shows no evidence of tumor 303 detected in the reference image slice. For example, the image slice in FIG. 3b shows normal tissues 311 and 312 that correspond to normal tissues 301 and 302, respectively, in the reference image slice, but the image slice in FIG. 3b does not show evidence of the tumor 303.

Figure 3C:
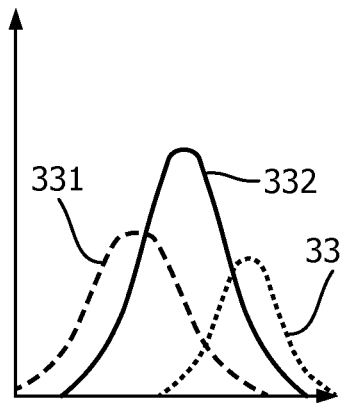
Figure 3D:
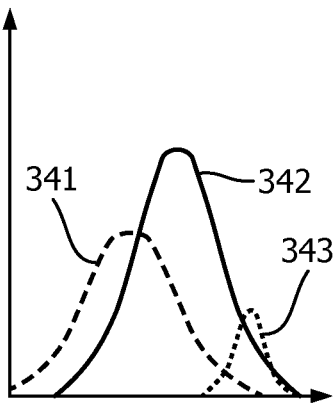
Figure 3E:
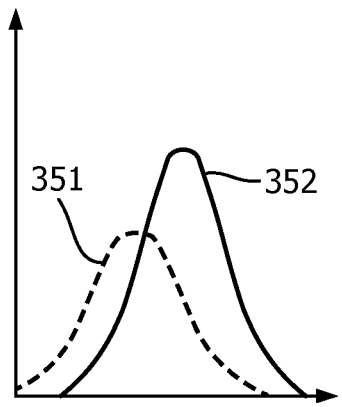

As another example, FIG. 3c shows an output of an image slice analysis performed on a reference image slice (e.g., an image slice in which tumor 333 was detected), and FIGS. 3d and 3e show outputs of an image slice analysis performed on image slices derived from a search of a reduced search space of image slices from other examinations. In one use case, the reference image slice in FIG. 3c may be associated with an examination at time t3, the image slice in FIG. 3d may be associated with an examination at time t2, and the image slice in FIG. 3e may be associated with an examination at time t1 (e.g., where time t1 is at least a predetermined threshold amount of time prior to time t2, time t2 is at least the predetermined threshold amount of time prior to t3, etc.). The reference image slice in FIG. 3c shows normal tissues 331 and 332 and tumor 333. The image slice in FIG. 3d shows normal tissues 341 and 342 (corresponding to normal tissues 331 and 332) along with tumor indication 343 of the tumor 333 detected in the reference image slice. If, for example, the time t2 examination occurred prior to the time t3 examination, tumor indication 343 may be evidence of the development of the tumor 333. Moreover, the image slice in FIG. 3e shows normal tissues 351 and 352 (corresponding to normal tissues 331 and 332), but no indication of the tumor 333. If, for example, the time t1 examination occurred prior to the time t2 examination, it may be determined that the development of the tumor 303 began sometime between time t1 and time t2.

In some embodiments, presentation component 114 may to provide information to one or more users and/or enable the users to interact with one or more user interface features. As an example, presentation component 114 may provide a representation of a finding in a given image slice (e.g., captured during a given examination of an individual), enable the user to select the given image slice as a reference image slice to be used for searching a database of image slices and/or processing of search results therefrom, provide representations of one or more indications of the finding in one or more other image slices of a search space, or provide other features. In some embodiments, presentation component 114 may provide, via a user interface, a representation of an indication of a finding (e.g., detected in a reference image slice) responsive to a determination that one or more indications of the detected finding exist in the image slices of a search space.

Figure 4A:
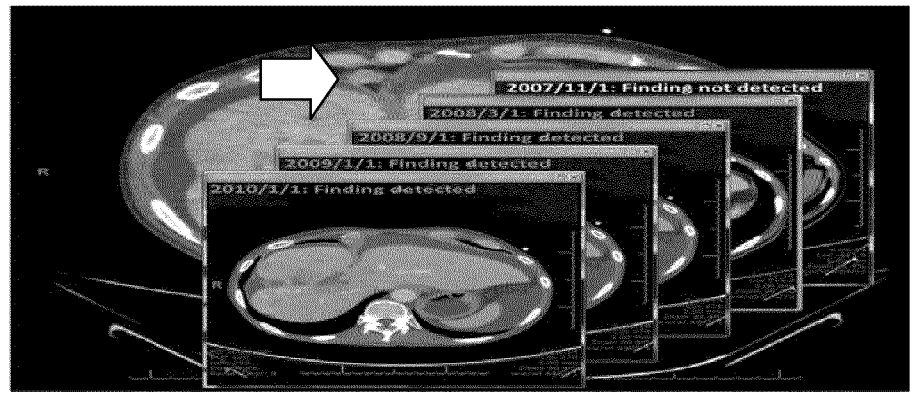
FIGS. 4a-4b illustrate a user interface presenting relevant image slices derived from an autonomous search of image slices, in accordance with one or more embodiments.
Figure 4B:
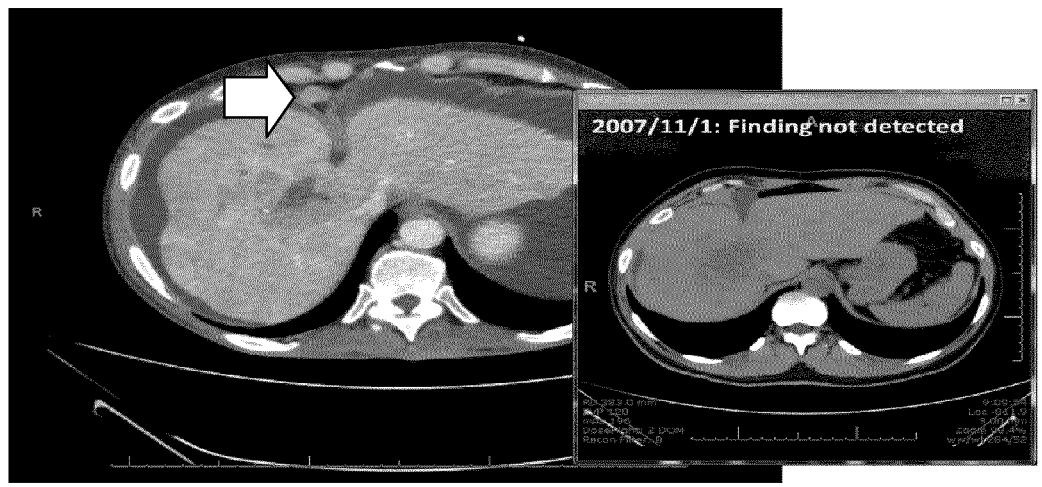

As an example, FIG. 4a shows a stacked ribbon presentation or cascade arrangement of registered slices found by the autonomous search of other examinations (e.g., prior examinations of the same individual). Each slice can be independently selected and visually highlighted including the slices having the marked finding detected and the slice having no finding just prior to the slice having the finding. As another example, FIG. 4b shows that by clicking a window of a particular outcome slice from the stack of outcome slices in FIG. 4b, the particularly chosen slice is enlarged and the other remaining windows disappear or decrease in size. This view allows instant comparison of new findings across a series of medical imaging studies.

In some embodiments, presentation component 114 may work with annotation component 112 to enable one or more users to annotate one or more pixels, voxels, or regions of one or more image slices. In some embodiments, annotation component 112 may perform automatic annotation of image slices using Picture Archiving Communication System (PACS) tools or similar tools to make basic annotations, such as measurements, circles, arrows, or other annotations. In some embodiments, annotation component 112 may perform automatic annotation of image slices using one or more recognition models (e.g., anatomy recognition models, disease-specific recognition models, etc.), or other models.

Figure 5:
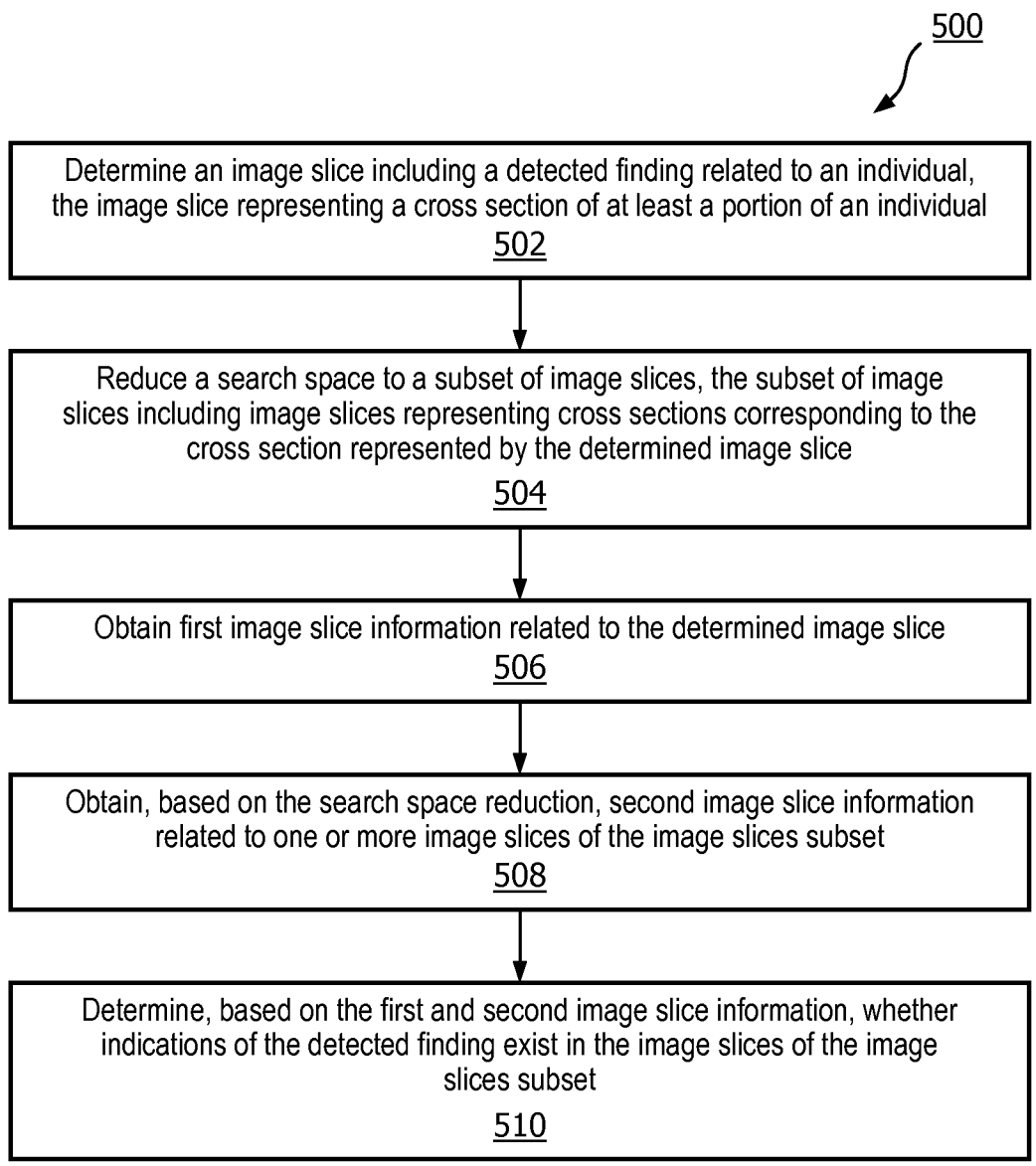
FIG. 5 illustrates a method for facilitating computer-assisted search of image slices for indications of a finding, in accordance with one or more embodiments.

FIG. 5 illustrates a method for facilitating computer-assisted search of image slices for indications of a finding, in accordance with one or more embodiments. The operations of method 500 presented below are intended to be illustrative. In some embodiments, method 500 may be accomplished with one or more additional operations not described, and/or without one or more of the operations discussed. Additionally, the order in which the operations of method 500 are illustrated in FIG. 5 and described below is not intended to be limiting.

In some embodiments, one or more operations of method 500 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 500 in response to instructions stored electronically on an electronic storage medium. The one or more processing devices may include one or more devices configured through hardware, firmware, and/or software to be specifically designed for execution of one or more of the operations of method 500.

At an operation 502, an image slice that includes a detected finding related to an individual may be determined. As an example, the determined image slice may represent a cross section of at least a portion of the individual (e.g., captured during an examination of the individual or other event). Operation 502 may be performed by one or more hardware processors 120 configured to execute a machine-readable instruction component that is the same as or similar to one or more of detection component 106, in accordance with one or more embodiments.

At an operation 504, a search space may be reduced to a subset of images. As an example, the subset of images may include image slices representing cross sections corresponding to the cross section represented by the determined image slice. The search space reduction may, for example, include filtering a set of image slices based on the cross section represented by the determined image slice. The set of image slices (that is filtered) may include image slices that respectively represent a cross section of at least a portion of the individual during one or more other examinations of the individual. Operation 504 may be performed by one or more hardware processors 120 configured to execute a machine-readable instruction component that is the same as or similar to one or more of search reduction component 108, in accordance with one or more embodiments.

In some embodiments, with respect to operation 504, the other examinations of the individual may include one or more prior examinations of the individual (e.g., that occurred at least a predetermined threshold amount of time prior to the examination of the individual during which the determined image slice was captured), one or more subsequent examinations of the individual (e.g., examinations occurring at least a predetermined threshold amount of time subsequent to the examination of the individual during which the determined image slice was captured), or other examinations of the individual. The foregoing operation(s) may be performed by one or more hardware processors 120 configured to execute a machine-readable instruction component that is the same as or similar to one or more of search reduction component 108, in accordance with one or more embodiments.

In some embodiments, with respect to operation 504, the other examinations may be selected from a set of examinations of the individual based on (i) a time of the examination (during which the determined image slice was captured), (ii) a time criteria (e.g., a time at which a selected examination was performed must have been at least a predetermined threshold amount of time from the given examination during which the determined image slice was captured or other time criteria), or (iii) other criteria. In some embodiments, the set of images (that is filtered to reduce the search space) may be selected based on each of the images of the image subset. The foregoing operation(s) may be performed by one or more hardware processors 120 configured to execute a machine-readable instruction component that is the same as or similar to one or more of search reduction component 108, in accordance with one or more embodiments.

In some embodiments, with respect to operation 504, the search space may be reduced to the image slices subset by filtering the image slices subset by (i) selecting a first image slice of the image slices subset based on the first image slice representing a cross section corresponding to the cross section represented by the determined image slice and (ii) selecting a second image slice of the image slices subset based on the second image slice being within a threshold proximity of the first image slice. In some embodiments, a region (including the detected finding) in the determined image slice may be determined. The threshold proximity (e.g., used to reduce the search space) may be based on information related to the region of the determined image size. The information related to the region may include size information associated with the region of the determined image slice, shape information associated with the region, location information associated with the region, or other information. As an example, the size information may include information identifying a size of the region of the determined image slice with respect to a first dimension, information identifying a size of the region of the determined image slice with respect to a second dimension different from the first dimension, or other information. The foregoing operation(s) may be performed by one or more hardware processors 120 configured to execute a machine-readable instruction component that is the same as or similar to one or more of search reduction component 108, in accordance with one or more embodiments.

At an operation 506, first image slice information related to the determined image slice may be obtained. Operation 506 may be performed by one or more hardware processors 120 configured to execute a machine-readable instruction component that is the same as or similar to one or more of image slice component 110, in accordance with one or more embodiments.

At an operation 508, second image slice information related to one or more image slices (of the image slices subset) may be obtained based on the reduced search space. Operation 508 may be performed by one or more hardware processors 120 configured to execute a machine-readable instruction component that is the same as or similar to one or more of image slice component 110, in accordance with one or more embodiments.

At an operation 510, a determination of whether one or more indications of the detected finding exist in the image slices of the image slices subset may be effectuated. Operation 510 may be performed by one or more hardware processors 120 configured to execute a machine-readable instruction component that is the same as or similar to one or more of image slice component 110, in accordance with one or more embodiments.

In some embodiments, system 100 includes one or more databases (e.g., examination database 116 or other databases), one or more computing platforms 104, one or more processors 120, electronic storage 122, external resources 118, and/or other components.

Examination database(s) 116 are configured to electronically store healthcare records of individuals and/or other information. As previously mentioned, the healthcare records may include a plurality of record attributes and corresponding values for the attributes.

In some embodiments, the databases (e.g., examination database 116) are associated with one or more entities such as medical facilities (e.g., hospitals, doctor's offices, etc.), healthcare management providers (e.g., a veteran's affairs medical system, a ministry of health, etc.), health insurance providers, and/or other entities. Databases 116 include electronic storage media that electronically stores information. In some embodiments, databases 116 are and/or are included in computers, servers, and/or other data storage systems associated with the one or more entities. The electronic storage media of databases 116 may include system storage that is provided integrally (i.e., substantially non-removable) with such systems. Databases 116 may include one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Databases 116 are configured to communicate with computing platforms 104, processor 120, electronic storage 122, external resources 118, and/or other components of system 100 such that the information stored by databases 116 may be accessed (e.g., as described herein) by other components of system 100 and/or other systems. It should be noted that use of the term "databases" is not intended to be limiting. A database may be any electronic storage system that stores healthcare records and allows system 100 to function as described herein.

Computing platforms 104 are configured to provide an interface between users and system 100. In some embodiments, computing platforms 104 are associated with databases 116, processor 120 and/or a server that includes processor 120, a healthcare provider, individual users associated with the healthcare provider, service providers (e.g., consultants) to the healthcare provider, individual users of system 100, and/or other users and/or entities. Computing platforms 104 are configured to provide information to and/or receive information from such users and/or entities. Computing platforms 104 include a user interface and/or other components. The user interface may be and/or include a graphical user interface configured to present views and/or fields configured to receive entry and/or selection of healthcare records and/or information associated with healthcare records, present information related to matched healthcare records (e.g., matching probabilities, F-scores, record attributes), and/or provide and/or receive other information. In some embodiments, the user interface includes a plurality of separate interfaces associated with a plurality of computing platforms 104, processors 120, and/or other components of system 100, for example.

In some embodiments, one or more computing platforms 104 are configured to provide a user interface, processing capabilities, databases, and/or electronic storage to system 100. As such, computing platforms 104 may include processors 120, electronic storage 122, external resources 118, and/or other components of system 100. In some embodiments, computing platforms 104 are connected to a network (e.g., the Internet). In some embodiments, computing platforms 104 do not include processor 120, electronic storage 122, external resources 118, and/or other components of system 100, but instead communicate with these components via the network. The connection to the network may be wireless or wired. For example, processor 120 may be located in a remote server and may wirelessly receive healthcare records for matching from one or more healthcare providers. In some embodiments, computing platforms 104 are laptops, desktop computers, smartphones, tablet computers, and/or other computing devices.

Examples of interface devices suitable for inclusion in the user interface include a touch screen, a keypad, touch sensitive and/or physical buttons, switches, a keyboard, knobs, levers, a display, speakers, a microphone, an indicator light, an audible alarm, a printer, and/or other interface devices. The present disclosure also contemplates that computing platforms 104 include a removable storage interface. In this example, information may be loaded into computing platforms 104 from removable storage (e.g., a smart card, a flash drive, a removable disk) that enables users to customize the embodiment of computing platforms 104. Other exemplary input devices and techniques adapted for use with computing platforms 104 and/or the user interface include, but are not limited to, an RS-232 port, RF link, an IR link, a modem (telephone, cable, etc.) and/or other devices.

As shown in FIG. 1, processor 120 is configured via machine-readable instructions to execute one or more computer program components. Processor 120 may be configured to execute components 106, 108, 110, 112, and/or 114 by software; hardware; firmware; some combination of software, hardware, and/or firmware; and/or other mechanisms for configuring processing capabilities on processor 120.

It should be appreciated that although components 106, 108, 110, 112, and 114 are illustrated in FIG. 1 as being co-located within a single processing unit, in embodiments in which processor 120 includes multiple processing units, one or more of components 106, 108, 110, 112, and/or 114 may be located remotely from the other components. The description of the functionality provided by the different components 106, 108, 110, 112, and/or 114 described below is for illustrative purposes, and is not intended to be limiting, as any of components 106, 108, 110, 112, and/or 114 may provide more or less functionality than is described. For example, one or more of components 106, 108, 110, 112, and/or 114 may be eliminated, and some or all of its functionality may be provided by other components 106, 108, 110, 112, and/or 114. As another example, processor 120 may be configured to execute one or more additional components that may perform some or all of the functionality attributed below to one of components 106, 108, 110, 112, and/or 114.

In the claims, any reference signs placed between parentheses shall not be construed as limiting the claim. The word "comprising" or "including" does not exclude the presence of elements or steps other than those listed in a claim. In a system claim enumerating several means, several of these means may be embodied by one and the same item of hardware. The word "a" or "an" preceding an element does not exclude the presence of a plurality of such elements. In any system claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system for facilitating computer-assisted search of image slices for indications of a finding, the system comprising:
one or more hardware processors configured by machine-readable instructions to:
determine an image slice that comprises a detected finding related to an individual, the determined image slice representing a cross section of at least a portion of the individual during an examination of the individual;
reduce a search space to a subset of image slices comprising image slices that respectively represent a cross section corresponding to the cross section represented by the determined image slice, wherein reducing the search space comprises filtering a set of image slices based on the cross section represented by the determined image slice, the image slices set comprising image slices that respectively represent a cross section of at least a portion of the individual during one or more other examinations of the individual, wherein the one or more other examinations of the individual comprises one or more prior examinations of the individual that occurred at least a predetermined threshold amount of time prior to the examination of the individual;
obtain first image slice information related to the determined image slice;
obtain, based on the search space reduction, second image slice information related to one or more image slices of the image slices subset; and
determine, based on the first image slice information and the second image slice information, whether one or more indications of the detected finding exist in the one or more image slices of the image slices subset.

2. The system of claim 1, wherein the one or more hardware processors are configured to provide, via a user interface, a representation of an indication of the detected finding responsive to a determination that one or more indications of the detected finding exist in the one or more image slices of the image slices subset.

3. The system of claim 1, wherein the first image slice information comprises information identifying characteristics related to the determined image slice, and the information identifying the characteristics related to the determined image slice comprises annotations associated with the determined image slice or characteristic vectors of objects represented in the determined image slice, and wherein the second image slice information comprises information identifying characteristics related to the one or more image slices of the image slices subset, and the information identifying the characteristics related to the one or more image slices comprises annotations associated with the one or more image slices or characteristic vectors of objects represented in the one or more image slices.

4. The system of claim 1, wherein the one or more hardware processors are configured to reduce the search space to the image slices subset by:
selecting the image slices set based on image slices of the image slices set being associated with the selected one or more other examinations; and
filtering the selected image slices set based on the cross section represented by the determined image slice by selecting at least one image slice of the image slices subset based on the at least one image slice representing a cross section corresponding to the cross section represented by the determined image slice such that the reduced search space comprises the at least one image slice.

5. The system of claim 1, wherein reducing the search space to the image slices subset comprises filtering the image slices subset by (i) selecting a first image slice of the image slices subset based on the first image slice representing a cross section corresponding to the cross section represented by the determined image slice and (ii) selecting a second image slice of the image slices subset based on the second image slice being within a threshold proximity of the first image slice.

6. The system of claim 5, wherein the one or more hardware processors are configured to:
determine, in the determined image slice, a region comprising the detected finding, the region being a portion of the determined image slice;
determine size information associated with the region of the determined image slice, the size information comprising information identifying a size of the region of the determined image slice with respect to a first dimension or information identifying a size of the region of the determined image slice with respect to a second dimension different from the first dimension; and
determine the threshold proximity based on the size information.

7. The system of claim 1, wherein the one or more hardware processors are configured to:
determine, in the determined image slice, a region comprising the detected finding, the region being a portion of the determined image slice; and
further reduce the search space by reducing the search space to one or more regions of the one or more image slices of the image slices subset based on the one or more regions corresponding to the region of the determined image slice,
wherein obtaining the first image slice information and the second image slice information is based on the further search space reduction.

8. A method of facilitating computer-assisted search of image slices for indications of a finding, the method comprising:
determining an image slice that comprises a detected finding related to an individual, the determined image slice representing a cross section of at least a portion of the individual during an examination of the individual;
reducing a search space to a subset of image slices comprising image slices that respectively represent a cross section corresponding to the cross section represented by the determined image slice, wherein reducing the search space comprises filtering a set of image slices based on the cross section represented by the determined image slice, the image slices set comprising image slices that respectively represent a cross section of at least a portion of the individual during one or more other examinations of the individual, wherein the one or more other examinations of the individual comprises one or more prior examinations of the individual that occurred at least a predetermined threshold amount of time prior to the examination of the individual;
obtaining first image slice information related to the determined image slice;
obtaining, based on the search space reduction, second image slice information related to one or more image slices of the image slices subset; and determining, based on the first image slice information and the second image slice information, whether one or more indications of the detected finding exist in the one or more image slices of the image slices subset.

9. The method of claim 8, wherein the method further comprises providing, via a user interface, a representation of an indication of the detected finding responsive to a determination that one or more indications of the detected finding exist in the one or more image slices of the image slices subset.

10. The system of claim 8, wherein the first image slice information comprises information identifying characteristics related to the determined image slice, and the information identifying the characteristics related to the determined image slice comprises annotations associated with the determined image slice or characteristic vectors of objects represented in the determined image slice, and wherein the second image slice information comprises information identifying characteristics related to the one or more image slices of the image slices subset, and the information identifying the characteristics related to the one or more image slices comprises annotations associated with the one or more image slices or characteristic vectors of objects represented in the one or more image slices.

11. The method of claim 8, wherein reducing the search space to the image slices subset comprises:
selecting the image slices set based on image slices of the image slices set being associated with the selected one or more other examinations; and
filtering the selected image slices set based on the cross section represented by the determined image slice by selecting at least one image slice of the image slices subset based on the at least one image slice representing a cross section corresponding to the cross section represented by the determined image slice such that the reduced search space comprises the at least one image slice.

12. The method of claim 8, wherein reducing the search space to the image slices subset comprises filtering the image slices subset by (i) selecting a first image slice of the image slices subset based on the first image slice representing a cross section corresponding to the cross section represented by the determined image slice and (ii) selecting a second image slice of the image slices subset based on the second image slice being within a threshold proximity of the first image slice.

13. The method of claim 12, further comprising:
determining, in the determined image slice, a region comprising the detected finding, the region being a portion of the determined image slice;
determining size information associated with the region of the determined image slice, the size information comprising information identifying a size of the region of the determined image slice with respect to a first dimension or information identifying a size of the region of the determined image slice with respect to a second dimension different from the first dimension; and
determining the threshold proximity based on the size information.

14. The method of claim 8, further comprising:
determining, in the determined image slice, a region comprising the detected finding, the region being a portion of the determined image slice; and
further reducing the search space by reducing the search space to one or more regions of the one or more image slices of the image slices subset based on the one or more regions corresponding to the region of the determined image slice,
wherein obtaining the first image slice information and the second image slice information is based on the further search space reduction.

15. A system for facilitating computer-assisted search of image slices for indications of a finding, the system comprising:
means for determining an image slice that comprises a detected finding related to an individual, the determined image slice representing a cross section of at least a portion of the individual during an examination of the individual;
means for reducing a search space to a subset of image slices comprising image slices that respectively represent a cross section corresponding to the cross section represented by the determined image slice, wherein reducing the search space comprises filtering a set of image slices based on the cross section represented by the determined image slice, the image slices set comprising image slices that respectively represent a cross section of at least a portion of the individual during one or more other examinations of the individual, wherein the one or more other examinations of the individual comprises one or more prior examinations of the individual that occurred at least a predetermined threshold amount of time prior to the examination of the individual;
means for obtaining first image slice information related to the determined image slice;
means for obtaining, based on the search space reduction, second image slice information related to one or more image slices of the image slices subset; and
means for determining, based on the first image slice information and the second image slice information, whether one or more indications of the detected finding exist in the one or more image slices of the image slices subset.

16. The system of claim 15,
wherein the system further comprises means for providing, via a user interface, a representation of an indication of the detected finding responsive to a determination that one or more indications of the detected finding exist in the one or more image slices of the image slices subset.

17. The system of claim 15, wherein reducing the search space to the image slices subset comprises:
selecting the image slices set based on image slices of the image slices set being associated with the selected one or more other examinations; and
filtering the selected image slices based on the cross section represented by the determined image slice by selecting at least one image slice of the image slices subset based on the at least one image slice representing a cross section corresponding to the cross section represented by the determined image slice such that the reduced search space comprises the at least one image slice.

18. The system of claim 15, further comprising:
means for determining, in the determined image slice, a region comprising the detected finding, the region being a portion of the determined image slice;
means for determining size information associated with the region of the determined image slice, the size information comprising information identifying a size of the region of the determined image slice with respect to a first dimension or information identifying a size of the region of the determined image slice with respect to a second dimension different from the first dimension; and means for determining the threshold proximity based on the size information, wherein reducing the search space to the image slices subset comprises filtering the image slices subset by (i) selecting a first image slice of the image slices subset based on the first image slice representing a cross section corresponding to the cross section represented by the determined image slice and (ii) selecting a second image slice of the image slices subset based on the second image slice being within a threshold proximity of the first image slice.

19. The system of claim 15, further comprising:

means for determining, in the determined image slice, a region comprising the detected finding, the region being a portion of the determined image slice; and means for further reducing the search space by reducing the search space to one or more regions of the one or more image slices of the image slices subset based on the one or more regions corresponding to the region of the determined image slice, wherein obtaining the first image slice information and the second image slice information is based on the further search space reduction.

* * * * *